United States Patent [19]

Igarashi

[11] Patent Number: 4,997,653
[45] Date of Patent: Mar. 5, 1991

[54] METHOD FOR TREATING ENDOMETRIOSIS WITH TOPICAL PREPARATIONS CONTAINING DANAZOL

[76] Inventor: Masao Igarashi, 357-4, Hiyoshi-cho H-chome, Maebashi-shi, Gunma, Japan

[21] Appl. No.: 287,481

[22] Filed: Dec. 20, 1988

[30] Foreign Application Priority Data

Mar. 1, 1988 [JP] Japan .................. 63-45928

[51] Int. Cl.$^5$ .................. A61F 6/06; A61F 13/00; A61K 31/58; A61K 31/74
[52] U.S. Cl. ............................ 424/433; 424/432; 424/484; 424/430; 424/78; 424/422; 424/486; 514/964; 514/967; 514/968; 514/176
[58] Field of Search .............. 424/432, 484, 422, 433, 424/430, 78, 486; 514/964, 967, 968, 176

[56] References Cited

U.S. PATENT DOCUMENTS

| | | | |
|---|---|---|---|
| 4,012,496 | 3/1977 | Schopflin et al. | 424/432 |
| 4,012,497 | 3/1977 | Schopflin | 424/432 |
| 4,016,251 | 4/1977 | Higuchi et al. | 424/432 |
| 4,115,563 | 9/1978 | John | 514/176 |
| 4,237,885 | 12/1980 | Wong et al. | 424/432 |
| 4,264,575 | 4/1981 | Zimmerman et al. | 424/432 |
| 4,286,587 | 9/1981 | Wong | 424/432 |
| 4,835,146 | 5/1989 | Harrington et al. | 514/176 |
| 4,837,212 | 6/1989 | Harrington et al. | 514/176 |

FOREIGN PATENT DOCUMENTS 0158277 10/1985 European Pat. Off. .

OTHER PUBLICATIONS

Ho et al., Systems Approach to Vaginal Delivery of Drugs, 11/26, vol. 65, #14, J. Pharm. Sci., 1578-1585.

*Primary Examiner*—Lester L. Lee
*Assistant Examiner*—Carmen Pili-Curtis
*Attorney, Agent, or Firm*—McGlew & Tuttle

[57] ABSTRACT

A topical preparation of danazol comprising a matrix base, danazol retained therein, and optionally a release-promoting agent is provided.

The topical preparation is more effective than oral administration of danazol in the shrinkage of endometriosis tissue, the induction of pregnancy, and the like. It does not show any side effects that have been encountered in the oral administration of danazol. Thus, the preparation is very useful remedy for endometriosis.

8 Claims, No Drawings

METHOD FOR TREATING ENDOMETRIOSIS WITH TOPICAL PREPARATIONS CONTAINING DANAZOL

BACKGROUND OF THE INVENTION

1. Field of the Invention

This invention relates to danazol-containing topical preparations which are markedly effective in the treatment of pelvic endometriosis and uterine adenomyosis. More particularly, it relates to intrauterine and vaginal preparations comprising a matrix base having danazol retained therein.

2. Description of the Prior Art

Endometriosis is a disease which occurs mostly in mature women and is frequently associated with infertility. According to the site of the focus, it is broadly divided into pelvic endometriosis (external endometriosis) and uterine adenomyosis (internal endometriosis).

Danazol is a drug which is highly estimated and widely used as an oral remedy for endometriosis ("Gekkan Yakuji", Vol. 25, No. 4, p. 691, 1983), but its effectiveness as a topical remedy has been unknown not only in Japan but also throughout the world. This seems to be due to the fact that two theories are being widely supported in connection with the mode of action of orally administered danazol. One of them is the worldwide established theory that orally administered danazol suppresses the function of the hypothalamo-hypophysial system to decrease the secretion of follicle-stimulating hormone (FSH) and luteinizing hormone (LH), resulting in decreased secretion of estrogens by the ovary and eventual shrinkage of endometriosis tissue (Fertility and Sterility, Vol. 29, p. 637, 1978). In other words, this theory insists that oral administration of danazol is the so-called pseudomenopausal therapy in which the functions of the ovary are suppressed completely. The other is a corrected theory which accepts the foregoing established theory in principle, but admits the presence of an appreciable direct effect on endometriosis cells (American Journal of Obstetrics and Gynecology, Vol. 140, p. 62, 1981).

Meanwhile, almost all women suffering from endometriosis become infertile. As pelvic endometriosis extends, menstrual pain appears and further aggravation results in a complaint of non-menstrual pain in the loins or lower abdomen. In cases of uterine adenomyosis, many patients complain of menstrual pain and hypermenorrhea in addition to infertility. Thus, most patients with endometriosis consult a doctor for medical advice about their infertility. It is only a few that complain chiefly of menstrual pain and have no desire for pregnancy in the future. In other words, the desire of most patients is the success of pregnancy, and the treatment of menstrual or non-menstrual pain is nothing but a secondary desire.

However, oral administration of danazol is ineffective in most cases of uterine adenomyosis. On the other hand, orally administered danazol is considerably effective for pelvic endometriosis, but has the following disadvantages. (1) The patient is utterly unable to conceive during and soon after the treatment because ovulation is suppressed. (2) The pregnancy rate after discontinuance of the treatment is low. (3) It is not rare that a recurrence of endometriosis occurs several months after discontinuance of the treatment.

As a result of intensive investigations made in view of these circumstances, the present inventor has unexpectedly found that (1) intrauterine application of danazol has a marked effect on uterine adenomyosis for which its oral administration has been virtually ineffective; (2) vaginal application of danazol does not suppress ovulation even during treatment and the patient may become pregnant even during treatment; (3) a high pregnancy rate is achieved as contrasted with oral administration; (4) prolonged vaginal application of danazol can prevent the recurrence of endometriosis which is often encountered after discontinuance of its oral administration; and (5) topical application of danazol is not associated with such side effects as are often encountered in its oral administration, including a weight gain, an aggravation of acne, a (transient) hepatic functional disorder and the like. Thus, the present inventor has first demonstrated the incorrectness of the conventionally established idea that the effect of danazol on endometriosis is produced by suppressing the endocrine functions of the hypothalamus-hypophysis-ovary system perfectly. The present invention has been completed on the basis of these findings.

SUMMARY OF THE INVENTION

The present invention has first clarified from a clinical point of view that, in danazol treatment, its direct effect on endometriosis cells exists undoubtedly and this direct effect is much more important than the suppressive effect on the hypothalamus-hypophysis-ovary system, and has also demonstrated the unreasonableness of the foregoing established and corrected theories in which the so-called pseudomenopausal therapy is considered to be the basis of danazol treatment. The present invention is the first instance of topical application of danazol not only in Japan but also throughout the world.

According to the present invention, there are provided topical preparations of danazol comprising a matrix base, i.e. a topical drug delivery system danazol retained therein, and optionally a release-promoting agent. These topical preparations of danazol will hereinafter be referred to briefly as the present preparations.

The shapes of the present preparations may be any of various shapes commonly employed for insertion into the uterus or vagina. Typically, the present preparations can be shaped like the letter T or Ota's ring when they are designed for insertion into the uterus, and can be shaped like an annular ring when they are designed for insertion into the vagina.

The sizes of the present preparations should be as follows: For T-shaped intrauterine preparations, the horizontal member has a length of 20 to 40 mm, preferably 30 to 35 mm, and a diameter of 1.0 to 3.0 mm, preferably 1.8 to 2.6 mm, and the vertical member has a length of 25 to 45 mm, preferably 30 to 38 mm, and a diameter of 3.0 to 4.0 mm, preferably 3.2 to 3.6 mm. For Ota's ring-like intrauterine preparations, they have an outer diameter of 20 to 25 mm and a ring thickness of 2.5 to 4.5 mm, preferably about 3.0 mm. For annular vaginal preparations, they have an outer diameter of 30 to 60 mm, preferably 45 to 55 mm, and a ring thickness of 4.0 to 12.0 mm, preferably 7.5 to 10.0 mm.

T-shaped or Ota's ring-like intrauterine preparations usually have a single-layer structure. However, in order to enhance their rigidity, they may have a two-layer structure in which a core comprising a piece of Silascon Rod (manufactured by Dow Corning Co.) or other material is embedded. Where a core is embedded in T-shaped intrauterine preparations, a satisfactory result can usually be obtained by embedding the core only in the horizontal member. The length of the core should be in the range of 55 to 70 % of the length of the horizontal member used, and the diameter of the core should be in the range of 60 to 90 % of the diameter of the horizontal member. In the case of T-shaped intrauterine preparations, it is necessary to attach a nylon monofilament to the lower end of the vertical member. This nylon monofilament should have a length of 30 to 400 mm, preferably 50 to 280 mm, and a diameter of 0.270 to 0.290 mm. On the other hand, annular vaginal preparations may be configured so as to have a single-layer or a two-layer structure, with a view to controlling the degree of release of the active component according to the duration of treatment and the severity of symptoms. However, where annular vaginal preparations have a two-layer structure, the outer layer should have as thickness of at lease 0.1 mm and preferably 0.1 to 2.0 mm.

The content of the active component, or danazol, in the present preparations may be in the range of dosage where, during topical application, the beneficial effects of danazol can manifest themselves according to the duration of treatment and the severity of symptoms. Specifically, the content of danazol should be in the range of 80 to 200 mg, preferably 100 to 180 mg, for intrauterine preparations and in the range of 50 to 4000 mg, preferably 90 to 3500 mg, for vaginal preparations. Where the content of danazol in vaginal preparations is selected to be as low as 1000 mg or less, it is desirable that they have a two-layer structure in which the outer layer has the selected content of danazol.

The present preparations should be made so as to have a composition comprising 20 to 50 parts by weight of the active component, or danazol, 50 to 80 parts by weight of the matrix base, and optionally 0.5 to 8 parts by weight of the release-promoting agent. Where the present preparations have a two-layer structure, it is necessary that the outer layer has the aforesaid composition without fail. The nucleus may comprise a core as defined above or a suitable material formed into any desired shape and size. The material used for this purpose may be of the same type as or a different type from the matrix base.

As described above, the present preparations contain danazol and a matrix base or topical drug delivery system as essential components and a release-promoting agent as an optional component. In addition to these components, they contain a very small amount of a vulcanization catalyst on the basis of their manufacturing method.

The matrix base used in the present preparations may be selected from various polymeric compounds which are widely used in intrauterine or vaginal drug delivery system and authorized for medical use. Specific examples thereof includes silicone rubber (polydimethylsiloxane), silicone-carbonate copolymer, ethylene-vinylacetate copolymer, ethylene-vinylalcohol copolymer, polyethylene, polymethyl methacrylate, polyhydroxyethyl methacrylate, polyisobutylene, polycarbonate, polybutylmethacrylate, natural gum, polyalkylcyanoacrylate, ethylcellulose, carboxymethylethylcellulose, polyethylene glycol, polyvinyl alcohol, carboxyvinyl polymer and collagen. However, polydimethylsiloxane, silicone-carbonate copolymer, ethylene-vinylacetate copolymer and ethylene-vinylalcohol copolymer are most preferred from the viewpoint of the retention and release of danazol. The term "matrix base" as used herein comprehend various types of matrix bases which may contain a cross-linking agent according to the need. The cross-linking agent may be any of various drug delivery systems that are commonly used according to the type of the matrix base. Commercial products of polydimethylsiloxane can be used for the aforesaid purpose, and typical examples thereof are MDX-4-4210 (containing a cross-linking agent) and Silastic 382 (both manufactured by Dow Corning Co.). The release-promoting agent which is used as an optional component may be selected from Polysorbate 60, Polysorbate 80, glycerol, isopropyl palmitate, isopropyl myristate and the like.

The present preparations can be made according to standard techniques for the manufacture of intrauterine or vaginal preparations. For example, single-layer preparations are made by charging danazol, a matrix base and, if desired, a release-promoting agent into a vessel placed in a clean bench, adding a vulcanization catalyst thereto, mixing these ingredients at room temperature for 2 to 30 minutes, pouring the resulting mixture into a mold, and solidifying it at room temperature. The contents or weight ratios of danazol, the matrix base and the release-promoting agent should be selected so as to fall within the aforesaid ranges and the mold should be one which gives the above-described shape and size. The vulcanization catalyst may comprise a tin catalyst or a platinum catalyst and should be used in an amount of 0.1 to 2.0 % by weight, preferably 0.5 to 1 % by weight, based on the amount of the matrix base. Two-layer preparations are made according to substantially the same procedure as described above for single-layer preparations, but it additionally includes the step of embedding a desired nucleus after pouring the mixture into the mold. The nucleus may comprise any of the above-described materials. Since the present preparations must be sterile products on the basis of their usage, they should be made under sterile conditions. It is to be understood that the final products thus obtained are packaged with heat-sealable aluminum packaging material.

DESCRIPTION OF THE PREFERRED EMBODIMENTS

The rate of release of danazol from the present preparations will be described hereinbelow. The rate of release was tested in two different ways, i.e., by in vitro tests and by clinical tests.

In Vitro Tests

A number of preparations made in accordance with the present invention were each suspended in 2 to 3 liters of distilled water and held at 37° C. for 8 to 44 days with stirring of the water. The amount of danazol released into the water per day was determined by liquid gas chromatography. During the test period, the distilled water was replaced every day.

The amount of danazol released per day was about 250 to 400 μg for intrauterine preparations and about 1000 to 3000 μg for vaginal preparations.

Clinical Tests

A number of preparations made in accordance with the present invention were each inserted into the uterus or vagina of 50 patients with endometriosis, aged 28 to 39, and retained therein for 2 to 30 weeks. The amount of release of danazol per day was determined by calculating the difference between the danazol contents of the preparation at the beginning and the end of the insertion, and dividing it by the number of days of insertion. The danazol content of each preparation was determined by extracting the preparation with chloroform and measuring the amount of danazol present in the extract by absorption photometry.

The amount of danazol released per day was about 150 to 300 μg for intrauterine preparations and about 900 to 3000 μg for vaginal preparations.

EXAMPLE 1 (VAGINAL PREPARATIONS)

(I) A vessel placed in a clean bench was charged with 20 g of danazol, 75 g of Silastic 382 and 5 g of Polysorbate 80. After the addition of 1.2 g of a tin catalyst, these ingredients were mixed at room temperature for 20 minutes. The resulting mixture was poured into three types of molds and solidified by allowing the molds to stand at room temperature for one day. Thus, there were obtained a total of 6 single-layer annular vaginal preparations as described below, two for each type.
(1) Danazol content: 2300 mg.
    Size: 55 mm in outer diameter, 9.5 mm in ring thickness.
(2) Danazol content: 2200 mg.
    Size: 52.5 mm in outer diameter, 9.5 mm in ring thickness.
(3) Danazol content 2100 mg.
    Size: 50 mm in outer diameter, 9.5 mm in ring thickness.

(II) The same procedure as described in paragraph (I) above was repeated, except that the amount of danazol was increased from 20 g to 30 g, the amount of Silastic 382 was decreased from 75 g to 70 g, and the addition of Polysorbate 80 was omitted. Thus, there were obtained a total of 6 single-layer annular vaginal preparations as described below, two for each type.
(1) Danazol content: 3500 mg.
    Size: 55 mm in outer diameter, 9.5 mm in ring thickness.
(2) Danazol content: 3300 mg.
    Size: 52.5 mm in outer diameter, 9.5 mm in ring thickness.
(3) Danazol content: 3200 mg.
    Size: 50 mm in outer diameter, 9.5 mm in ring thickness.

EXAMPLE 2 (VAGINAL PREPARATIONS)

Using a mixture composed of 55 g of MDX-4-4210 (containing a cross-linking agent) and 0.5 g of a platinum catalyst, core rings having an outer diameter of 48.5 mm and a thickness of 5.5 mm were prepared in advance.

Thus, 15 g of danazol, 38.5 g of MDX-4-4210 (containing a cross-linking agent) and 0.35 g of a platinum catalyst were mixed at room temperature for 30 minutes. The resulting mixture was poured into molds and the previously prepared core rings were embedded therein. The mixture was solidified by allowing the molds to stand at room temperature for one day. Thus, there were obtained 6 two-layer annular vaginal preparations as described below. These preparations had an outer layer of 2.0 mm thickness.
Danazol content: 2200 mg.
Size: 52.5 mm in outer diameter, 9.5 mm in ring thickness.

EXAMPLE 3 (INTRAUTERINE PREPARATIONS)

(I) In a vessel placed in a clean bench, 3.00 g of danazol, 11.25 g of Silastic 382 and 0.5 g of Polysorbate 80 were mixed. After the addition of 0.18 g of a tin catalyst, the mixing was continued for 15 minutes. The resulting mixture was poured into molds and solidified by allowing the molds to stand at room temperature for one day. Thus, there were obtained 20 single-layer T-shaped intrauterine preparations as described below. A nylon monofilament was attached when the mixture was poured into each mold.
Danazol content: 116 mg.
Size:
    Horizontal member; 32 mm in length, 2.6 mm in diameter.
    Vertical member; 36 mm in length, 3.6 mm in diameter.
    66-nylon monofilament: 54 mm in length, 0.285 mm in diameter.

(II) The same procedure as described in paragraph (I) above was repeated, except that the amount of danazol was increased from 3.00 g to 4.5 g, the amount of Silastic 382 was decreased from 11.25 g to 10.5 g, and the addition of Polysorbate 80 was omitted. Thus, there were obtained 20 single-layer T-shaped intrauterine preparations as described below.
Danazol content: 175 mg.
Size:
    Horizontal member; 32 mm in length, 2.6 mm in diameter.
    Vertical member; 32 mm in length, 3.6 mm in diameter.
    Yellow nylon monofilament: 280 mm in length, 0.277 mm in diameter.

(III) The same procedure as described in paragraph (II) above was repeated, except that a core comprising a piece of Silascon Rod having a length of 20 mm and a diameter of 1.6 mm was embedded in the mixture poured into each mold. Thus, there were obtained 20 two-layer T-shaped intrauterine preparations as described below.
Danazol content: 108 mg.
Size:
    Horizontal member; 32 mm in length, 1.8 mm in diameter.
    Vertical member; 32 mm in length, 3.2 mm in diameter.
    Yellow nylon monofilament: 250 mm in length, 0.277 mm in diameter.

EXAMPLE 4 (INTRAUTERINE PREPARATIONS)

1.5 g of danazol, 3.5 g of Silastic 382 and an appropriate amount of a tin catalyst were mixed at room temperature for 10 minutes. The resulting mixture was poured into molds in which a core ring comprising a ring of Silascon Rod having an outer diameter of 20.5 mm and a thickness of 1.6 mm was placed. The mixture was solidified by allowing the molds to stand for one day. Thus, there were obtained 10 two-layer Ota's ring-like intrauterine preparations as described below.
Danazol content: 90 mg.
Size: 22 mm in outer diameter, 3.0 mm in ring thickness.

EFFECTS OF THE INVENTION

The effects of the present preparations on endometriosis will be more fully described hereinbelow. The description will be separately given with respect to cases of pelvic endometriosis (external endometriosis) and cases of adenomyosis (internal endometriosis).

Pelvic Endometriosis

In 46 patients, aged 28–37, who had been diagnosed as cases of pelvic endometriosis, a vaginal preparation made in the same manner described in Example 1 was inserted into the vagina for purposes of treatment. These 46 cases included 32 cases in which oral administration of danazol had been found to be ineffective. The period of treatment was up to 30 weeks and the site of insertion of the preparation was around the opening of the uterus.

(1) Effect on endometriosis tissue in the uterine culde-sac

In all of the 46 cases, a marked decrease of endometriosis tissue in the uterine cul-de-sac was noted. Specifically, in 12 cases in which the size (or area) of the tissue was 10–12 $cm^2$ at the start of the treatment, it was reduced to 2–3 $cm^2$ in the 2nd week. Similarly, 31 cases showed a reduction from 6–8 $cm^2$ to 0.5–3 $cm^2$ in the 4th to 8th week, and 1 case showed a reduction from 3 $cm^2$ to 1 $cm^2$ in the 4th week. In the 12th to 17th weeks, the size of the tissue was reduced to 0–0.5 $cm^2$ in all of these 44 cases. In the other 2 cases (in which the size of the tissue was 8 $cm^2$ or 6 $cm^2$ at the start of the treatment), the size of endometriosis tissue in the cul-de-sac was not reduced to 0.5 $cm^2$ or less by the 12th to 17th week. The reason why no improvement was observed in these cases seems to be that, since they had adhesive retroflexion of the uterus due to endometriosis in the cul-de-sac and the treatment brought about shrinkage and softening of the endometriosis tissue, the fundus of the uterus could be directly touched by bimanual examination, resulting in an increased volume of palpable tissue. The degree of effectiveness was 100 %.

(2) Effect on tenderness in the uterine cul-de-sac

An improvement of tenderness in the cul-de-sac was noted in all of the 46 cases. A complete cure was achieved in 33 cases, and the average time required for the complete cure was 17.2 weeks. In the other 13 cases, the tenderness was not completely cured, but ameliorated. In one case observed for 17 weeks, pregnancy resulted from homologous artificial insemination (AIH). The degree of effectiveness was 100 %.

(3) Effect on menstrual pain

Menstrual pain was completely cured in 32 out of the 46 cases and ameliorated in 11 cases. The average time required for the amelioration of pain was 5.3 weeks and the average time required for the complete disappearance of pain was 14.3 weeks. The degree of effectiveness was 93.5 %.

(4) Effect on non-menstrual pain in the lower abdomen or loins.

Of the 46 cases, 20 complained of non-menstrual pain in the lower abdomen or loins at the start of the treatment. In all of these cases, the pain disappeared in an average of 6.7 weeks. The other 26 cases did not complain of such pain at the start of the treatment. The degree of effectiveness was 100 %.

(5) Induction of pregnancy

Of the 46 cases, 11 became pregnant during insertion of the vaginal preparation of the present invention. The pregnancy resulted from sexual intercourse in 10 cases and from homologous artificial insemination in the other one. It is quite surprising that, in contrast to oral administration of danazol during which the patient never becomes pregnant, the vaginal preparations of the present invention allowed the patient to become pregnant even during treatment. In consideration of the above-described results and the fact that these patients had failed to conceive for the past several years, it is evident that (1) the patients being treated with the present preparations are not only able to conceive, but more likely to conceive than before treatment and (2) even during treatment, ovulation is not suppressed and spermatozoa are not prevented from passing through the cervical mucus. The degree of effectiveness was 24 %. Just after confirming the establishment of pregnancy, the vaginal ring was removed. They all delivered normal babies with no congenital anomaly.

(6) Other effects

In all of the 46 cases, neither suppression of ovulation nor decrease in blood FSH or LH was noted during treatment. Moreover, the present preparations did not show such side effects as are encountered in the oral administration of danazol, including a weight gain, an aggravation of acne, an increase of GOT and GPT, and the like.

Uterine Adenomyosis

In 4 patients, aged 34–39, who had been diagnosed as cases of uterine adenomyosis, an intrauterine preparation made in the same manner described in Example 3 was inserted into the uterus for purposes of treatment. These 4 cases included one case in which oral administration of danazol had been found to be ineffective. The period of treatment was up to 4 months and the site of insertion of the preparation was within the uterus.

(1) Effect on the corpus of the uterus

In all of the 4 cases, a marked reduction in size of the corpus of the uterus was noted. The length of time required for the onset of shrinkage of the corpus of the uterus was within 2 weeks in all cases. The degree of effectiveness was 100 %.

(2) Effect on menstrual pain

In all of the 4 cases, an amelioration of menstrual pain was noted in an average of 7 weeks after the start of the treatment. Of these case, 3 were completely cured (i.e., the pain disappeared completely) in an average of 14.6 weeks. The degree of effectiveness was 100 %.

(3) Effect on non-menstrual pain in the lower abdomen or loins

At the start of the treatment, 3 out of the 4 cases complained of non-menstrual pain in the lower abdomen or loins. In all of these 3 cases, the pain disappeared in an average of 6.6 weeks. The degree of effectiveness was 100 %.

(4) Induction of pregnancy

Of the 4 cases, 2 became pregnant immediately after removal of the intrauterine preparation of the present invention. The degree of effectiveness was 50 %.

As described above, the present preparations are more effective than oral administration of danazol in the shrinkage of endometriosis tissue, the induction of pregnancy, and the like. Moreover, they do not show any side effects that have been encountered in the oral administration of danazol. Accordingly, it may safely be said that the present preparations are novel and very useful remedies for endometriosis.

I claim:

1. A method of treating endometriosis comprising a topical pharmaceutical composition of danazol comprising a matrix base topical drug delivery system and an effective amount of danazol retained therein.

2. Method of claim 1 wherein said endometriosis is pelvic endometriosis or adenomyosis.

3. Method of claim 1 wherein said preparation is inserted into a uterine cavity.

4. Method of claim 1 wherein said preparation is inserted into a vagina.

5. A method of treating endometriosis comprising a topical pharmaceutical composition of danazol comprising a matrix base topical drug delivery system and an effective amount of danazol retained therein, and release-promoting agent.

6. A method as claimed in claim 5 wherein said endometriosis is pelvic endometriosis or adenomyosis.

7. A method as claimed in claim 5 wherein said preparation is inserted into a uterine cavity.

8. A method as claimed in claim 5 wherein said preparation is inserted into a vagina.

* * * * *